United States Patent
DiSalvo et al.

(10) Patent No.: US 8,636,860 B2
(45) Date of Patent: Jan. 28, 2014

(54) IONIC LIQUID MONOPROPELLANT GAS GENERATOR

(75) Inventors: Roberto DiSalvo, Madison, AL (US); H. Waite Dykes, Jr., Huntsville, AL (US); Robin D. Rogers, Tuscaloosa, AL (US); Julia Shamshina, Tuscaloosa, AL (US); Marcin Smiglak, Bad Friedrichshall (DE)

(73) Assignees: Streamline Automation, LLC, Huntsville, AL (US); The University of Alabama, Tuscaloosa, AL (US)

( * ) Notice: Subject to any disclaimer, the term of this patent is extended or adjusted under 35 U.S.C. 154(b) by 309 days.

(21) Appl. No.: 12/958,022

(22) Filed: Dec. 1, 2010

(65) Prior Publication Data

US 2012/0138859 A1  Jun. 7, 2012

Related U.S. Application Data

(60) Provisional application No. 61/266,024, filed on Dec. 2, 2009.

(51) Int. Cl.
| | | |
|---|---|---|
| *C06B 47/00* | (2006.01) | |
| *C06B 47/08* | (2006.01) | |
| *C06B 25/00* | (2006.01) | |
| *C06B 25/34* | (2006.01) | |
| *D03D 23/00* | (2006.01) | |
| *D03D 43/00* | (2006.01) | |

(52) U.S. Cl.
USPC ... 149/1; 149/36; 149/88; 149/92; 149/109.2; 149/109.4

(58) Field of Classification Search
USPC .............. 149/1, 36, 88, 92, 109.2, 109.4
See application file for complete search history.

(56) References Cited

U.S. PATENT DOCUMENTS

| | | | |
|---|---|---|---|
| 3,871,828 A | | 3/1975 | Ellion et al. |
| 4,124,538 A | * | 11/1978 | Armstrong et al. ............ 502/332 |
| 5,485,722 A | * | 1/1996 | Schmidt et al. ................. 60/219 |
| 6,218,577 B1 | * | 4/2001 | Brand et al. .................... 564/464 |
| 6,509,473 B1 | * | 1/2003 | Drake ........................ 548/262.2 |
| 7,645,883 B1 | * | 1/2010 | Hawkins et al. .............. 548/255 |
| 7,745,635 B1 | | 6/2010 | Drake et al. |
| 2005/0269001 A1 | * | 12/2005 | Liotta et al. ....................... 149/1 |

FOREIGN PATENT DOCUMENTS

WO  2006078275 A2  7/2006

\* cited by examiner

*Primary Examiner* — James McDonough
(74) *Attorney, Agent, or Firm* — KIPA AB; Tomas Friend

(57) ABSTRACT

An energetic ionic liquid catalytic decomposition gas generator uses stoichiometric and nonstoiciometric mixtures of specific energetic ionic liquids and iridium catalyst. The catalyst temperature used and gas production versus ignition may be controlled by combining one or more cationic species with one or more anionic species of the ionic liquid(s).

12 Claims, No Drawings

IONIC LIQUID MONOPROPELLANT GAS GENERATOR

CROSS-REFERENCE TO RELATED APPLICATIONS

This application is a non-provisional of and claims priority under 35 U.S.C. 119(e) to U.S. provisional application Ser. No. 61/266,024.

STATEMENT REGARDING FEDERALLY SPONSORED RESEARCH

The U.S. Government has certain rights to this invention pursuant to Contract No.: W911NF-08-C-0080 awarded by the US Army.

BACKGROUND OF THE INVENTION

1. Field of the Invention

The present invention relates to single propellant gas generators. More specifically, the invention is an energetic ionic liquid monopropellant; a gas generator comprising the energetic ionic liquid monopropellant and a metal catalyst; and a method for generating a gas in which an energetic ionic liquid monopropellant is contacted with a metal catalyst.

2. Description of Related Art

In a catalytic, monopropellant gas generator, a monopropellant is contacted with a catalyst that causes the monopropellant to rapidly decompose, usually without causing monopropellant combustion. Hot gas produced by the catalytic decomposition of a monopropellant may be used, for example, to drive a turbine of an emergency generator providing electricity. Combustion of the monopropellant in a gas generator must normally be avoided because combustion temperatures are high enough to irreversibly inactivate the catalyst and/or damage the gas generator and/or the turbine. Therefore, combinations of monopropellant, catalyst, and operating conditions are desired that rapidly produce large amounts of hot gas without ignition.

Monopropellant gas generators based on hydrazine and iridium catalyst are described in U.S. Pat. No. 3,871,828; U.S. Pat. No. 4,324,096; and U.S. Pat. No. 4,490,972. Hydrazine is a powerful but toxic and volatile monopropellant. Less toxic and/or less volatile alternatives to hydrazine monopropellant, including some ionic liquids, have been made. These ionic liquids are not useful for many existing gas generator applications, however, because of poor thermal stability or failure to perform as expected under required operating conditions. Consequently, there remains a need in the art for a reliable gas generator using a less toxic and/or less volatile alternative to hydrazine.

U.S. Pat. No. 6,218,577 to Brand et al. discloses the synthesis of specific energetic, hydrazinium salts, including hydroxyethylhydrazinium (HEH) nitrate salts and indicates that the salts are useful as a replacement for hydroxylammonium nitrate (HAN) in monopropellant fuels for propulsion and gas generators. The '577 patent does not provide any examples of or conditions required for the use of HEH nitrate salt monopropellant.

U.S. Pat. No. 5,485,722 to Schmidt et al. discloses the catalytic decomposition of HAN by platinum group or transition metal group catalysts including 32% iridium on alumina, 12% rhodium on alumina, 10% platinum on alumina, 12% ruthenium on alumina, and platinum/titanium sheet catalyst. The '722 patent discloses that the controlled catalytic HAN decomposition is preferably conducted at a temperature of between 80° C. and 120° C. The rate of HAN decomposition is controlled and combustion and detonation of HAN requires choking of the exit flow from a reactor in a sonic flow nozzle as well as controlling the flow of monopropellant over the catalyst.

U.S. Pat. No. 7,745,635 to Drake et al. and U.S. Pat. No. 6,509,473 to Drake disclose energetic ionic liquids including 4-amino-1,2,4-triazolium nitrate and that the energetic ionic liquids should have applications as monopropellants and gas generators. The '635 patent makes no mention of catalytic decomposition or conditions under which 4-amino-1,2,4-triazolium salts might be used as catalytic decomposition monopropellants.

US 2005/0269001 discloses energetic ionic liquids useful as monopropellants for propulsion and gas generators but does not mention catalysts or conditions for the use of any energetic ionic liquids for gas generation.

BRIEF SUMMARY OF THE INVENTION

The present invention fills a need in the art for a reliable gas generator using monopropellant that is less hazardous and less toxic than hydrazine. The gas generated by the gas generator may be used, for example, to pressurize a fuel tank, drive a turbine, inflate an airbag, or provide thrust.

The present invention arises, in part, from the unexpected discovery that HEH nitrate salts do not react with the same catalysts or under the same conditions as HAN or hydrazine as one would predict based upon the state of the art. Experimentation revealed that HEH nitrate salts do not react with most of the catalysts known for the catalytic decomposition of HAN or hydrazine. Further experimentation additionally revealed that the stoichiometry, i.e. the cation to anion ratio influences both the temperature at which HEH nitrates decomposes on iridium catalyst as well as the vigor with which they decompose.

The present invention also arises, in part, from the discovery that ionic liquids other than HEH nitrate, including HEH chlorides and 4-amino-1,2,4-triazolium nitrates are also useful as energetic ionic liquid monopropellants in catalytic decomposition gas generators. Additionally, the conditions under which these ionic liquids react with catalysts differs from conditions and catalysts used with HAN, hydrazine, and HEH nitrate. The discoveries described herein enable the control of the catalyst temperature required to initiate, and of the rate of, ionic liquid monopropellant decomposition by varying the ratios of various cationic and anionic species in an ionic liquid monopropellant.

DETAILED DESCRIPTION OF THE INVENTION

A gas generator according to the present invention comprises a storage tank containing an energetic ionic liquid monopropellant and a reaction chamber containing an iridium metal catalyst, an inlet configured to receive energetic ionic liquid from the storage tank, and an outlet configured to release a gas from the reaction chamber. A corresponding method for generating a gas comprises the step of contacting an energetic ionic liquid monopropellant with an iridium metal catalyst.

The term "ionic liquid" used herein refers to salts (i.e., compositions comprising cations and anions) that are liquid at a temperature of at or below about 150° C. That is, at one or more temperature ranges or points at or below about 150° C. the disclosed ionic liquid compositions are liquid; although, it is understood that they can be solids at other temperature ranges or points. Energetic ionic liquids of the present invention are 2-hydroxyethylhydrazinium and 4-amino-1,2,4-triazolium cations combined with nitrate, chlorides, chlorate, perchlorate, dicyanamide, nitrite, sulfate, and sulfite anions and mixtures thereof. The energetic ionic liquid may contain non-integer ratios of cations and non-integer ratios of specific and/or total cation to anion.

Synthesis of Energetic Ionic Liquids

Example 1

2-hydroxyethylhydrazinium (HEH) nitrate

HEH nitrate, $[HO(CH_2)_2NHNH_3]^+NO_3^-$, was synthesized as follows:
2-hydroxyethyl hydrazine (15 mmol, 1.140 g) was placed in a 20 mL glass vial fitted with a magnetic stir bar. 2-hydroxyethyl hydrazine was chilled in an ice bath and Nitric acid (15 mmol), aqueous solution, was then added dropwise. The vial was capped and the reaction mixture was stirred overnight. The water was then removed by means of air stream and the resulting material was additionally dried in a 50° C. furnace. The pure compound has a glass transition temperature of −56.9° C. with an onset to 5% decomposition of 193° C.

Example 2

2-hydroxyethylhydrazinium (HEH) dinitrate

HEH dinitrate $[HO(CH_2)_2NH_2NH_3]^{+2}2NO_3^-$, was synthesized as follows:
2-hydroxyethyl hydrazine (15 mmol, 1.140 g) was placed in a 20 mL glass vial fitted with a magnetic stir bar. 2-hydroxyethyl hydrazine was chilled in an ice bath and Nitric acid (30 mmol), aqueous solution, was then added dropwise. The vial was capped and the reaction mixture was stirred overnight. The water was then removed by means of air stream and the resulting material was additionally dried in a 50° C. furnace. The pure compound is a waxy solid at room temperature with a melting point of 67° C. with an onset to 5% decomposition of 62° C.

No reaction was observed during prolonged contact of HEH nitrate or HEH dinitrate with stainless steel or oxygen-free copper, which are commonly used as structural materials for gas generators, storage tanks, and fuel lines.

Example 3

4-amino-1,2,4-triazolium nitrate 4-amino-1,2,4-triazolium nitrate was synthesized as follows:
4-amino-1,2,3-triazole (0.841 g, 10 mmols) was placed in a 20 mL glass vial fitted with a magnetic stir bar. Compound was chilled in an ice bath and nitric acid (10 mmol), aqueous solution, was then added dropwise. The vial was capped and the reaction mixture was stirred overnight. The water was then removed by means of air stream and the resulting material was additionally dried in a 50° C. furnace.

Example 4

4-amino-1,2,4-triazolium dinitrate 4-amino-1,2,4-triazolium dinitrate was synthesized as follows:
4-amino-1,2,3-triazole (0.841 g, 10 mmols) was placed in a 20 mL glass vial fitted with a magnetic stir bar. Compound was chilled in an ice bath and nitric acid (20 mmol), aqueous solution, was then added dropwise. The vial was capped and the reaction mixture was stirred overnight. The water was then removed by means of air stream and the resulting material was additionally dried in a 50° C. furnace.

Example 5

2-hydroxyethylhydrazinium (HEH) chloride

HEH chloride, $[HO(CH_2)_2NHNH_3]^+Cl^-$, was synthesized as follows:
2-hydroxyethyl hydrazine (15 mmol, 1.140 g) was placed in a 20 mL glass vial fitted with a magnetic stir bar. Hydrochloric acid (15 mmol), aqueous solution, was then added. The vial was capped and the reaction mixture was stirred overnight. The water was then removed by means of air stream and the resulting material was additionally dried in a 50° C. furnace.

Example 6

2-hydroxyethylhydrazinium (HEH) dichloride

HEH dichloride, $[HO(CH_2)_2NH_2NH_3]^{+2}Cl^{-2}$, was synthesized as follows:
2-hydroxyethyl hydrazine (15 mmol, 1.140 g) was placed in a 20 mL glass vial fitted with a magnetic stir bar. Hydrochloric acid (30 mmol), aqueous solution, was then added. The vial was capped and the reaction mixture was stirred overnight. The water was then removed by means of air stream and the resulting material was additionally dried in a 50° C. furnace.

Ionic Liquid-Catalyst Combinations:

HEH nitrate and HEH dinitrate were contacted with Palladium on Carbon, Samarium powder, Iron metal, AlNi (Raney® Nickel), Platinum metal, Indium metal, and Iridium on alumina catalysts at room temperature. Surprisingly, HEH nitrate and dinitrate decomposition occurred only when contacted with Iridium on alumina catalyst. Contrary to what one would expect based upon known catalytic decomposition gas generator monopropellants and catalysts, all but one of the catalysts tested failed to initiate HEH nitrate and HEH dinitrate decomposition.

Iridium-on-Alumina Catalyst:

Testing was performed using Shell 405® catalyst containing 32% Iridium on alumina and another catalyst containing 24% Iridium on alumina with five energetic ionic liquids at 100° C. and 200° C. One drop of ionic liquid at room temperature was placed on a sample of each catalyst and observed for several minutes. The results are summarized in Table 1 and Table 2. Commercial Shell 405® catalyst contains 31% to 35% Iridium metal by weight.

TABLE 1

| Ionic Liquids with Catalysts at 100° C. | | |
|---|---|---|
| Ionic Liquid | 32% Iridium | 24% Iridium |
| 2-HEH nitrate | vigorous reaction | slight reaction |
| 2-HEH dinitrate | vigorous reaction | slight reaction |
| 2-HEH chloride | reaction | no reaction |
| 2-HEH dichloride | reaction | no reaction |
| 4-amino-1,2,4-triazolium nitrate | no reaction | no reaction |

TABLE 2

Ionic Liquids with Catalysts at 200° C.

| Ionic Liquid | 32% Iridium | 24% Iridium |
|---|---|---|
| 2-HEH nitrate | ignition | reaction |
| 2-HEH dinitrate | ignition | slight reaction |
| 2-HEH chloride | vigorous reaction | slight reaction |
| 2-HEH dichloride | reaction | slight reaction |
| 4-amino-1,2,4-triazolium nitrate | vigorous reaction | slight reaction |

HEH nitrate and HEH dinitrate at room temperature rapidly decompose when contacted with 32% Iridium catalyst at 100° C. without ignition. When contacted with Iridium catalyst at 200° C., however, the compounds ignite. HEH nitrate and HEH dinitrate stored at room temperature are therefore suitable for use in a gas generation with a 32% iridium catalyst on alumina at 100° C. but not at 200° C. HEH chloride and 4-amino-1,2,4-triazolium nitrate are suitable for use in a gas generator at 200° C. but not at 100° C. because the reaction is not vigorous at the lower temperature. 24% Iridium on alumina catalyst is not suitable for use with the ionic liquid monopropellants tested at a temperature of 200° C. or lower because none of the monopropellants react sufficiently when contacted with this catalyst. Mixtures containing combinations of less reactive and more reactive ionic liquid monopropellants may be formulated to provide desired reaction characteristics with iridium catalyst at a selected temperature to avoid ignition at the selected temperature, for example. Similarly, the temperature of an iridium catalyst may be adjusted to provide desired reaction characteristics for a selected ionic liquid monopropellant or monopropellant mixture.

Reactivity of 1:1 and 1:2 HEH:Nintrate Ratios at Elevated Temperature

Ionic liquids HEH nitrate or HEH dinitrate were added dropwise to 32% Iridium on alumina catalyst preheated to temperatures of 50° C., 100° C., 150° C., or 200° C. Unlike the conditions used for experiments summarized in Tables 1 and 2, the ionic liquids were preheated to the same temperatures as the catalyst before being contacted with the catalyst. No significant reaction occurred with either of the ionic liquids at 50° C. The results for 100° C., 150° C., or 200° C. are summarized in Table 3.

TABLE 2

HEH Nitrates with 32% Iridium Catalyst at 100° C., 150° C., and 200° C. Delay/Smoke time:time to start/duration of gas production after contact with catalyst.

| HEH:Nitrate Ratio Temperature | Delay time (ms) | Smoke time (ms) | Ignition |
|---|---|---|---|
| 1:1 100° C. | 1166 | 4558 | no |
| 1:1 150° C. | 90 | 1826 | yes |
| 1:1 200° C. | 114 | 2556 | yes |
| 1:2 100° C. | 582 | 4690 | yes |
| 1:2 150° C. | 28 | 5614 | yes |
| 1:2 200° C. | 162 | 1242 | yes |

Preheating HEH nitrates to the catalyst temperature increases their reactivity. HEH dinitrate is a waxy solid at room temperature and begins to decompose near its melting point, making it most suitable in combinations with lower melting point ionic liquids to increase their reactivity.

Varying Ratios of Ionic Liquid Cation to Anion:

Non-integer (nonstoicheometric) ratios of HEH cation to Nitrate anion unexpectedly provide certain advantages over 1:1 and 1:2 ratios of HEH:Nitrate. For example, HEH:Nitrate ratios may be varied to prevent the ignition of the monopropellant in a catalytic gas generator initially operating at a selected catalyst temperature. HEH:Nitrate ratios of 1:1.2 and 1:1.4 are hypergolic liquids when contacted with an 32% Iridium catalyst at 150° C., while HEH:Nitrate 1:1 is not hypergolic when contacted with 32% Iridium catalyst on alumina at 150° C. Neutral HEH does not react when contacted with 32% Iridium on alumina catalyst. Table 4 shows the observed results of reactions between variable HEH:Nitrate ratio compositions with 32% Iridium on alumina catalyst at 150° C. The reactions consumed all of the ionic liquid, leaving only traces of residue.

TABLE 4

Results of 32% Iridium catalyst - Catalyzed Reactions of HEH:Nitrate Ratios at 150° C. Delay/Smoke time:time to start/duration of gas production after contact with catalyst.

| HEH:Nitrate Ratio | Delay time (s) 1st drop; 2nd drop | Smoke time (s) 1st drop; 2nd drop | Ignition 1st drop; 2nd drop |
|---|---|---|---|
| 1:1 | 0; 0.6 | 2.7; 8.3 | no; no |
| 1:1.2 | 0; 0 | 3.2; 3.1 | yes; yes |
| 1:1.4 | 0; 0 | 1.8; 2.3 | yes; yes |
| 1:1.6 | 0; 0 | 8.0; 9.0 | yes; yes |
| 1:1.8 | 0; 0 | 8.1; 11.0 | yes; yes |

Compounds having HEH:Nitrate ratios of 1:1.6 and 1:1.8 are waxy solids at room temperature and hypergolic with 32% Iridium on alumina catalyst at 150° C. When compounds having HEH:Nitrate ratios of 1:1.6 and 1:1.8 at room temperature are contacted with 32% Iridium on alumina catalyst at 150° C., a few seconds elapse before they melt. Delay and Smoking times are measured from the point at which the ionic liquid has melted. While higher nitrate ratios are more energetic, a HEH:nitrate ratio of 1:1 is more fluid and thermally stable than HEH:nitrate ratio of 1:2.

Adjusting the ratio of HEH:Nitrate provides the unexpected advantage of controlling the whether the catalytic reaction at 150° C. is hypergolic (resulting in spontaneous ignition) or whether the catalytic reaction is a decomposition reaction without combustion. HEH cation to nitrate anion ratios at temperatures between 50° C. and 100° C. may be controlled to provide vigorous reaction without ignition because varying the ratio of HEH to nitrate allows one to control the temperature at which an Iridium-catalyzed decomposition reaction is hypergolic. Increasing the ratio raises the temperature required for ignition while lowering the ratio lowers the temperature requires for ignition. In the case of a gas generator, ignition is to be avoided so lowering the ratio of HEH to Nitrate provides one way of preventing ignition. Similarly, ionic liquid monopropellant cations and anions may be combined to produce monopropellant mixtures that prevent ignition with an iridium catalyst at a selected temperature.

While the present invention is described in terms of gas generation, it should be clear that the ionic liquid monopropellants may be intentionally formulated to result in ignition or detonation of the monopropellant when contacted with iridium catalyst in a combustion chamber to provide propulsion, for example.

The invention claimed is:

1. A gas generator comprising a storage tank containing an energetic ionic liquid and a reaction chamber comprising an iridium catalyst,
   wherein:
   said reaction chamber comprises an inlet configured to receive said energetic ionic liquid from the storage tank such that said energetic ionic liquid contacts and reacts with said catalyst and thereby decomposes said energetic ionic liquid to produce a gas,
   said reaction chamber comprises an outlet configured to release a gas from the reaction chamber, and
   said energetic ionic liquid is selected from the group consisting of 2-hydroxyethylhydrazinium nitrate, 2-hydroxyethylhydrazinium dinitrate, 2-hydroxyethylhydrazinium chloride, 2-hydroxyethylhydrazinium dichloride, 4-amino-1,2,4-triazolium nitrate, 4-amino-1,2,4-triazolium dinitrate, and mixtures thereof.

2. The gas generator of claim 1, wherein the iridium catalyst comprises 31% to 35% iridium metal on alumina.

3. The gas generator of claim 1, wherein the energetic ionic liquid is a mixture of 2-hydroxyethylhydrazinium nitrate and 2-hydroxyethylhydrazinium dinitrate and wherein the ratio of hydroxyethylhydrazinium ions to nitrate ions ranges from 1:1.1 to 1:1.9.

4. The gas generator of claim 3, wherein the ratio of hydroxyethylhydrazinium ions to nitrate ions ranges from 1:1.2 to 1:1.4.

5. The gas generator of claim 1, wherein the reaction chamber further comprises a heater configured to heat the catalyst and/or the reaction chamber.

6. The gas generator of claim 1, wherein:
   the energetic ionic liquid comprises 2-hydroxyethylhydrazinium dinitrate,
   said catalyst comprises from 32% to 35% Iridium metal by weight, and
   said catalyst has a temperature greater than 50° C. and less than 150° C. when said energetic ionic liquid contacts and reacts with said catalyst.

7. The gas generator of claim 1, wherein said energetic ionic liquid, said catalyst, and a catalyst temperature are selected such that gas is produced without ignition of said energetic ionic liquid.

8. The gas generator of claim 7, wherein said energetic ionic liquid comprises a mixture of 2-hydroxyethylhydrazinium nitrate and 2-hydroxyethylhydrazinium dinitrate, the catalyst temperature is selected to be between 50° C. and 150° C., and the catalyst comprises Iridium.

9. The gas generator of claim 7, wherein the energetic ionic liquid comprises 2-hydroxyethylhydrazinium nitrate, said catalyst contains 24% Iridium by weight, and said catalyst has a temperature of at least 200° C. when said energetic ionic liquid contacts and reacts with said catalyst.

10. The gas generator of claim 1, wherein the energetic ionic liquid comprises 2-hydroxyethylhydrazinium chloride, 4-amino-1,2,4-triazolium nitrate, or a combination thereof; said catalyst contains at least 32% Iridium by weight; and said catalyst has a temperature of at greater than 100° C. when energetic ionic liquid contacts and reacts with said catalyst.

11. The gas generator of claim 1, wherein catalyst temperature is greater than 100° C. said energetic ionic liquid comprises 2-hydroxyethylhydrazinium nitrate, 2-hydroxyethylhydrazinium dinitrate, or a combination thereof.

12. The gas generator of claim 1, wherein said energetic ionic liquid comprises 2-hydroxyethylhydrazinium dinitrate mixed with an ionic liquid having a melting point of less than 67° C.

* * * * *